(12) United States Patent
Chen et al.

(10) Patent No.: US 8,590,406 B2
(45) Date of Patent: Nov. 26, 2013

(54) MILLIMETER-WAVE RECEIVING DEVICE

(75) Inventors: Zhiqiang Chen, Beijing (CN); Yuanjing Li, Beijing (CN); Ziran Zhao, Beijing (CN); Yinong Liu, Beijing (CN); Wanlong Wu, Beijing (CN); Xilei Luo, Beijing (CN); Zhimin Zheng, Beijing (CN); Dong Lin, Beijing (CN); Zongjun Shen, Beijing (CN); Shuo Cao, Beijing (CN)

(73) Assignees: Tsinghua University, Beijing (CN); Nuctech Company Limited, Beijing (CN)

( * ) Notice: Subject to any disclaimer, the term of this patent is extended or adjusted under 35 U.S.C. 154(b) by 280 days.

(21) Appl. No.: 13/126,047

(22) PCT Filed: Dec. 28, 2010

(86) PCT No.: PCT/CN2010/080371
§ 371 (c)(1),
(2), (4) Date: Apr. 26, 2011

(87) PCT Pub. No.: WO2011/079779
PCT Pub. Date: Jul. 7, 2011

(65) Prior Publication Data
US 2012/0011947 A1 Jan. 19, 2012

(30) Foreign Application Priority Data
Jun. 30, 2010 (CN) .......................... 2010 1 0223337

(51) Int. Cl.
*G01N 23/00* (2006.01)
(52) U.S. Cl.
USPC ........................................................ 73/866.5
(58) Field of Classification Search
None
See application file for complete search history.

(56) References Cited

U.S. PATENT DOCUMENTS

| 3,433,953 | A | * | 3/1969 | Sweet et al. | ............... 250/336.1 |
| 3,499,153 | A | * | 3/1970 | Stanfill | ...................... 250/341.6 |
| 3,725,930 | A | | 4/1973 | Caruso, Jr. | |
| 3,854,336 | A | * | 12/1974 | Bibby | .......................... 374/124 |

(Continued)

FOREIGN PATENT DOCUMENTS

| CN | 1247320 | 3/2000 |
| CN | 1737512 | 2/2006 |
| CN | 1882200 | 12/2006 |
| CN | 101608997 | 12/2009 |
| GB | 406453 | 3/1934 |

OTHER PUBLICATIONS

First Office Action (in Chinese) for Chinese Application No. 201010223337.0, issued Aug. 27, 2012, 4 pages.

(Continued)

*Primary Examiner* — Robert R Raevis
(74) *Attorney, Agent, or Firm* — Westman, Champlin & Koehler, P.A.

(57) ABSTRACT

Disclosed is a millimeter-wave receiving device. The device includes at least one radiometer; and a positioning assembly for holding the radiometer, wherein the positioning assembly comprises: a first positioning member having a first surface; a second positioning member having a second surface, the first surface of the first positioning member and the second surface of the second positioning member holding the radiometer in opposite to each other. With the configuration according to the present invention, the at least one radiometer in the millimeter-wave receiving device can be located in all of freedoms on basis of various design requirements of the radiation path to ensure that the radiometer can be arranged in desired receiving positions.

15 Claims, 4 Drawing Sheets

(56) References Cited

U.S. PATENT DOCUMENTS

| | | | |
|---|---|---|---|
| 4,910,409 A * | 3/1990 | Hoffman et al. | 250/526 |
| 5,739,903 A * | 4/1998 | Kepner | 356/216 |
| 2005/0063447 A1 | 3/2005 | Ammar | |
| 2005/0237061 A1 | 10/2005 | Cloutier et al. | |
| 2006/0221330 A1 * | 10/2006 | Waldo et al. | 356/213 |
| 2011/0030728 A1 * | 2/2011 | Semmer et al. | 134/18 |

OTHER PUBLICATIONS

Extended European Search Report for PCT Application No. PCT/CN2010/080371, dated Oct. 18, 2012, 6 pages.

Search Report and Written Opinion from corresponding International Application No. PCT/CN2010/080371, dated Apr. 7, 2011.

* cited by examiner

MILLIMETER-WAVE RECEIVING DEVICE

CROSS-REFERENCE TO RELATED APPLICATION

This application is a Section 371 National Stage Application of International Application No. PCT/CN2010/080371, filed 28 Dec. 2010, not yet published which claims the benefit of Chinese Patent Application No. 201010223337.0 filed on Jun. 30, 2010 in the State Intellectual Property Office of China, the disclosure of which are incorporated herein by reference.

BACKGROUND OF THE INVENTION

1. Field of the Invention

The present invention relates to a millimeter-wave receiving device, and in particular, to a millimeter-wave receiving device for use in a human body millimeter-wave inspection apparatus.

2. Description of the Related Art

As well known in the art, a conventional human body security inspection apparatus generally comprises a metal detector, a trace analyzer, X-ray transmission apparatus. The metal detector is only sensitive to metal substances. The trace analyzer is only effective to drugs and explosives. The X-ray transmission apparatus can detect metal/non-metal matters, explosives, drugs, and so on. Although the X-ray transmission apparatus can have a high spatial resolution and a certain scanning speed, its application for the human body security inspection is limited as the ionizing radiation of the X-ray proves harmful to human body.

Recently, the millimeter-wave is catching people's attention in the area of human body security inspection as it has low radiation energy. In the circumstance where the millimeter-wave is used in the human body security inspection, it is possible to significantly reduce the damage of the radiation to the human body during the security inspection in addition to the detection and examination on the contraband articles concealed with the human body.

In an application for the human body security inspection with the millimeter-wave, a receiving device for the millimeter-wave radiation is very critical. The conventional millimeter-wave receiving devices are those used in the applications of wireless communication, guidance for a missile, electronic countermeasure and so on. They have high cost and complicated construction, and thus they are not suitable for use in the area of the human body security inspection.

It is desired to provide a receiving device for the millimeter-wave, which can be used in the millimeter-wave human body security inspection apparatus.

SUMMARY OF THE INVENTION

The object of the present invention is to provide a compact millimeter-wave receiving device in which the at least one radiometer can be located in all of freedoms on basis of various design requirements of the radiation path to ensure that the radiometer can be arranged in desired receiving positions.

Further, the present invention can reduce a thermal drift of the millimeter-wave receiving device and prevent undesired electrical-magnetic interference to improve the measuring accuracy of the radiometer. The present invention can further achieve a precise adjustment of a pitch angle of the radiometer.

In accordance with an aspect of the present invention, there is provided a millimeter-wave receiving device, comprising: at least one radiometer; and a positioning assembly for holding the radiometer, wherein the positioning assembly comprises: a first positioning member having a first surface; a second positioning member having a second surface, the first surface of the first positioning member and the second surface of the second positioning member holding the radiometer in opposite to each other.

In accordance with a further aspect of the present invention, the millimeter-wave receiving device comprises a plurality of one radiometers arranged in a line.

In accordance with a further aspect of the present invention, the first surface of the first positioning member is formed with a bulged border at its periphery, the bulged border comprising an upper rim and a lower rim, which are formed with at least one group of saw-shaped steps opposed to each other respectively; and wherein each radiometer includes a positioning portion which matches with its corresponding saw-shaped step, each radiometer being held on the saw-shaped step by the positioning portion.

In accordance with a further aspect of the present invention, each saw-shaped step has a first step positioning surface and a second step positioning surface, wherein the first step positioning surfaces of the respective saw-shaped steps are inclined at a same angle with respect to the horizontal direction, and wherein the second step positioning surfaces of the respective saw-shaped steps are inclined at a same angle with respect to the vertical direction.

In accordance with a further aspect of the present invention, each saw-shaped step has a first step positioning surface and a second step positioning surface, wherein the first step positioning surfaces of the respective saw-shaped steps are inclined at different angles with respect to the horizontal direction, and wherein the second step positioning surfaces of the respective saw-shaped steps are inclined at different angles with respect to the vertical direction.

In accordance with a further aspect of the present invention, the positioning portion is a limited step or a projection.

In accordance with a further aspect of the present invention, the first positioning member further has a third surface opposed to the first surface and the second positioning member has a fourth surface opposed to the second surface, wherein the third surface and the fourth surface are provided with a plurality of radiating fins thereon respectively.

In accordance with a further aspect of the present invention, the millimeter-wave receiving device further comprises partitions, which enclose the radiating fins provided on the third surface and the fourth surface respectively to form air passages.

In accordance with a further aspect of the present invention, a fan is provided at the inlet side or outlet side of the air passages, and an air vent, which corresponds to the fan, is arranged on the positioning assembly external to the fan.

In accordance with a further aspect of the present invention, the millimeter-wave receiving device further comprises: a supporting member; and an orientation assembly by which the positioning assembly is connected to the supporting member to adjust a pitch angle of the radiometer relative to the supporting member.

In accordance with a further aspect of the present invention, the orientation assembly further comprises: a connection member, one end of which is connected to the positioning assembly, and the other end of which is adjustably connected to the supporting member; and an arc-shaped slide opening provided on the supporting member, wherein the connection member connects the supporting member with the positioning assembly through the arc-shaped slide opening, and is capable of sliding in the arc-shaped slide opening to adjust the pitch angle of the radiometer with respect to the supporting member.

In accordance with a further aspect of the present invention, the first positioning member further comprises an extension portion provided with holes to which the connection member is connected through the arc-shaped slide opening.

In accordance with a further aspect of the present invention, the extension portion extends along the direction perpendicular to the first surface of the positioning member from one end of the first positioning member.

In accordance with a further aspect of the present invention, the millimeter-wave receiving device further comprises a shielding cylinder which surrounds the positioning assembly and the radiometer except a gap in the receiving direction of the radiometer, the shielding cylinder being supported on the positioning assembly by stands disposed on the positioning assembly.

In accordance with a further aspect of the present invention, the millimeter-wave receiving device further comprises: a high frequency amplifier and a high frequency amplifier bracket for fixing the high frequency amplifier, wherein the high frequency amplifier bracket having a grid arrangement in which each grid accommodates one high frequency amplifier.

In accordance with a further aspect of the present invention, the millimeter-wave receiving device further comprises a data sampling board mounded on the positioning assembly.

With the above configuration, the following advantages are at least provided:

1) The millimeter-wave receiving device has a compact structure and a reduced size and the radiometer can be accurately and precisely oriented in various directions;

2) An enclosed internal air passages is employed for reducing external thermal interference, thus improving the precision of the radiometer;

3) a shielding cylinder with a gap in the radiation receiving direction is used for avoiding the external electrical-magnetic interference;

4) An orientation assembly is used for adjusting the pitch angle of the radiometer accurately.

DETAILED DESCRIPTION OF THE EMBODIMENTS

Figure 1:
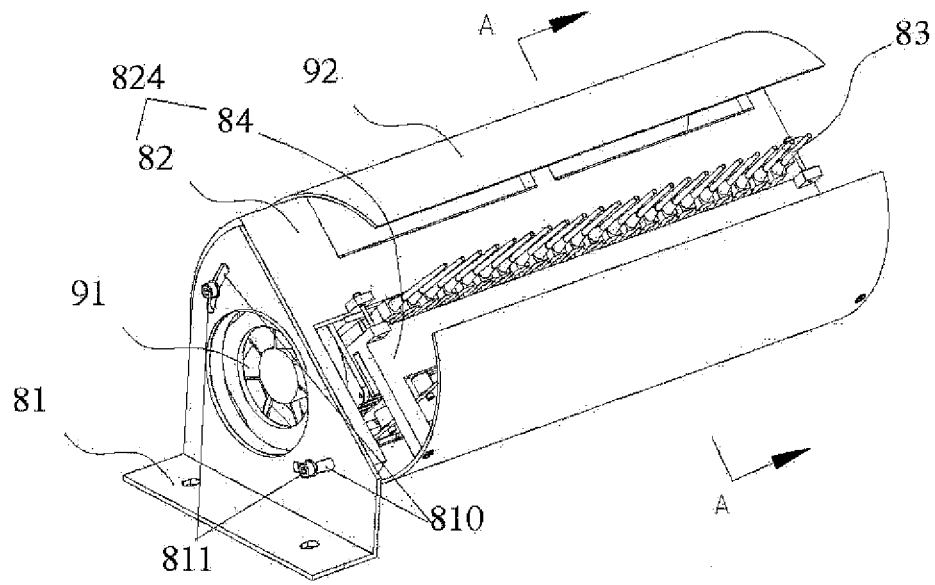
FIG. 1 is a perspective view showing a millimeter-wave receiving device according to an embodiment of the present invention.

Specific embodiments of the present invention will be described hereinafter in detail with reference to the accompanying drawings. In the drawings, like reference numerals refer to like parts. The embodiments are described below in order to explain the general concept of the present invention without limitations on the scope of the invention.

In a millimeter-wave human body inspection apparatus, it is desired to scan the human body by a specific radiation path and receive the millimeter-wave signals emitted from the respective parts of the human body. Thus, it is necessary for the radiation receiving device to have a function of positioning the radiometer accurately in the millimeter-wave human body inspection apparatus.

FIG. 1 illustrates an example of the millimeter-wave receiving device used in the millimeter-wave human body security inspection apparatus. The millimeter-wave receiving device may comprise at least one radiometer 83 and a positioning assembly 824 for fixing the radiometer 83. The positioning assembly 824 may further comprise a first positioning member 82 and a second positioning member 84. The first positioning member 82 may have a first surface 821 and the second positioning member 84 may have a second surface 841. The first and second surfaces 821, 841 may be used to fix the radiometer 83 in opposite to each other. In a typical embodiment, one, two or more radiometers 83 may be used. If a plurality of radiometers is provided, they may be arranged in a line.

The at least one radiometer 83 is held by the first positioning member 82 and the second positioning member 84. The first surface 821 and the second surface 841 are in contact with two opposed sides of the radiometer 83. The first and second positioning members 82, 84 may be connected by fasteners, such as bolts, to allow the first surface 821 and the second surface 841 to abut against the radiometer 83. In such arrangement, the radiometer 83 can be held stably towards the receiving direction of the millimeter-wave radiation.

In the case that the radiometers 83 are arranged in a line, barrier members, for example limiting blocks, may be provided at two ends of the line to prevent the radiometers 83 from shifting along the direction parallel to the first surface 821 or the second surface 841. In practice, if the shifting of the radiometers along the direction parallel to the first surface 821 or the second surface 841 is not limited, the radiometer 83 may be deviated from the radiation receiving direction, in particular, once the connection of the first positioning member 82 and the second positioning member 84 becomes slightly loose due to, for example, vibrations.

Figure 3:
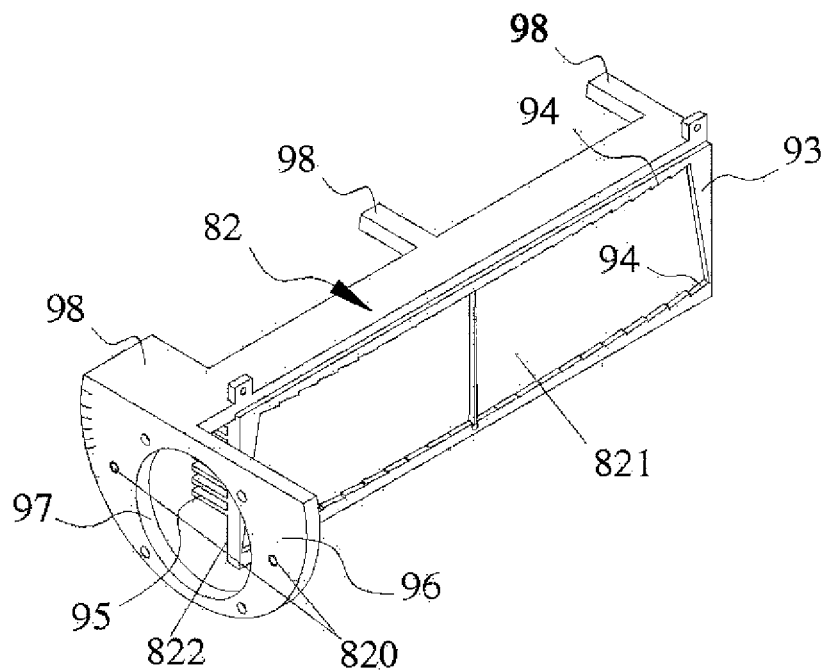
FIG. 3 is a perspective view showing a first positioning member according to an embodiment of the present invention.

In an embodiment, the first positioning member 82 is provided with a specific arrangement in order to avoid the movement and deflection of the radiometers parallel to the first surface 821 or the second surface 841. In an example, as illustrated in FIG. 3, a bulged border 93 is formed at periphery of the first surface 821 of the first positioning member 82. The bulged border 93 comprises an upper rim and a lower rim, which are formed with at least one group of saw-shaped steps 94 opposed to each other respectively. The respective saw-shaped steps 94 on the upper rim correspond to those on the lower rim. Each radiometer 83 includes a positioning portion 831 which matches its corresponding saw-shaped step 94. The radiometer 83 can be held on the saw-shaped step 94 by the positioning portion 831. Each of the saw-shaped steps 94 has two intersected positioning surfaces, i.e., a first step positioning surface and a second step positioning surface, which may delimit the displacement of the radiometer 83 in two directions and the rotation of the radiometer in a plane parallel to the first surface 821 or the second surface 841.

Figure 3A:
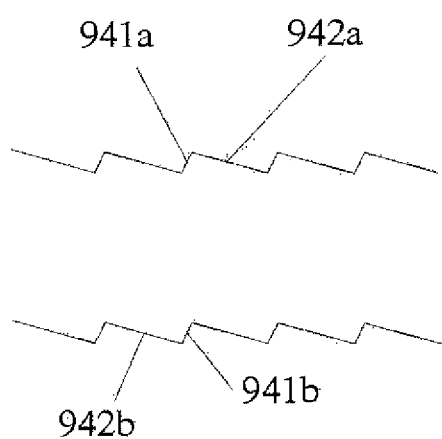
FIG. 3a is a schematic view showing the first and second step-like positioning surfaces of the first positioning member according to an embodiment of the present invention.

FIG. 3a shows schematically the first step positioning surface 941a and the second step positioning surface 942a of the saw-shaped step 94 on the upper rim and the first step positioning surface 941b and the second step positioning surface 942b of the saw-shaped step 94 on the lower rim. For a pair of corresponding saw-shaped steps 94, the first step positioning surface 941a and the second step positioning surface 942a face to the first step positioning surface 941b and the second step positioning surface 942b. These four step positioning surfaces can delimit the displacement and rotation of the radiometer 83 in the plane parallel to the first surface 821 or the second surface 841. At the same time, they may further delimit the displacement and rotation of the radiometer 83 in all spatial degrees of freedom in combination with the first surface 821 of the first positioning member 82 and the second surface 841 of the second positioning member 84.

Figure 6:
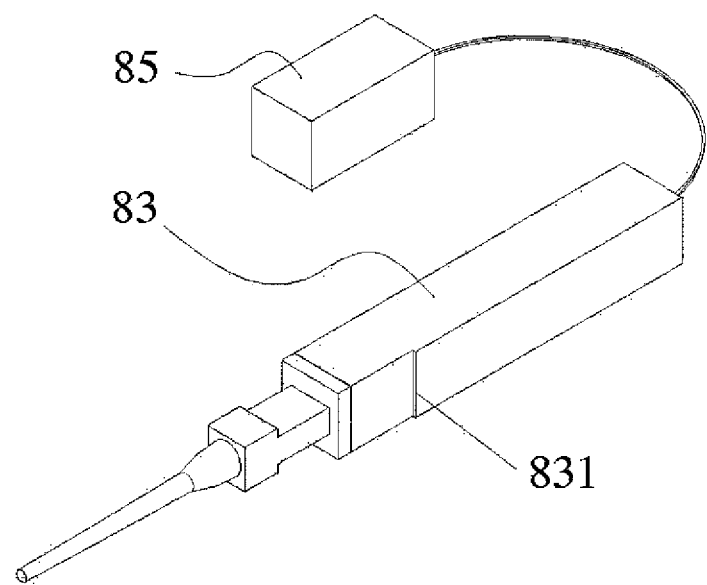
FIG. 6 is a perspective view showing a single radiometer and its corresponding high frequency amplifier according to an embodiment of the present invention.

The positioning portion 831 of the radiometer 83 may be for example a limited step or a projection, as shown in FIG. 6, however, other variations are also possible as long as it can be fitted to the step positioning surfaces of the saw-shaped steps 94. The dimension of the radiometer, in particular, the positioning portion 831 is designed to match with those of the projected borders 93 and the saw-shaped steps 94 to ensure that the radiometer 93 can be positioned correctly.

The first step positioning surfaces 941a, 941b and the second step positioning surfaces 942a, 942b may be horizontal or vertical respectively, or may be inclined at an angle, for example, 0~10 degrees with respect to the horizontal or vertical direction. The angle shown in FIG. 3a is only illustrative. The first step positioning surfaces 941a, 941b of the respective saw-shaped steps 94 may be inclined at a same angle with respect to the horizontal direction. The second step positioning surfaces 942a, 942b of the respective saw-shaped steps 94 may also be inclined at a same angle with respect to the vertical direction. In this way, the radiometer 83 held on the saw-shaped steps 94 will also be inclined in light of the step positioning surfaces.

Furthermore, when a plurality of radiometers 83 is provided, the respective first step positioning surfaces 941a, 941b may be arranged at different angles relative to the horizontal direction and the respective second step positioning surfaces 942a, 942b may be arranged at different angles relative to the vertical direction, to allow the respective radiometers to have radiation receiving directions angled to each other instead of parallel to each other, in order to adjust the radiation receiving directions of the respective radiometers 83 accurately. In an example, the inclination angles of the respective first step positioning surfaces 941a, 941b or the respective second step positioning surfaces 942a, 942b of the saw-shaped steps 94 may gradually increase or decrease from one lateral rim of the bulged borders 93 towards the other, or may gradually increase or decrease from the lateral rims of the bulged borders 93 towards the central rim of the bulged borders 93.

In an example, in FIG. 3, the bulged border 93 is divided into two parts by an intermediate member, and the above inclination angles gradually increase or decrease from the lateral rims of the bulged borders 93 towards the central rim of the bulged borders 93. Thus, the radiometers 83 on the bulged borders have radiation receiving directions which varies symmetrically from the lateral rims towards the central rim. This proves advantageous when receiving the millimeter-wave from an object to be inspected having a curve surface, and the imaging of the object can be improved.

As appreciated by the skilled person in the art, in the above embodiments in which the four step positioning surfaces 941a, 941b, 942a, 942b and the first surface 821 and the second surface 841 are used to locate the radiometer 83, it is not necessary for all of these positioning surfaces to contact with the radiometer 83. A gap can be maintained between some of these positioning surfaces and the radiometer as long as it meets requirement of desired tolerances.

The detection of the millimeter-wave is sensitive to the variation of the temperature, thus a radiating arrangement may be provided in the positioning assembly 824. For example, in an embodiment, a plurality of radiating fins 95 may be arranged on a third surface 822 of the first positioning member 82 and a fourth surface 842 of the second positioning member 84 respectively. The third surface 822 may be arranged on the first positioning member 82 in opposite to the first surface 821, and the fourth surface 842 may be arranged on the second positioning member 84 in opposite to the second surface 841. The radiating fins 95 may be directed or angled to the direction vertical to the third surface 822 and the fourth surface 842.

Figure 2:
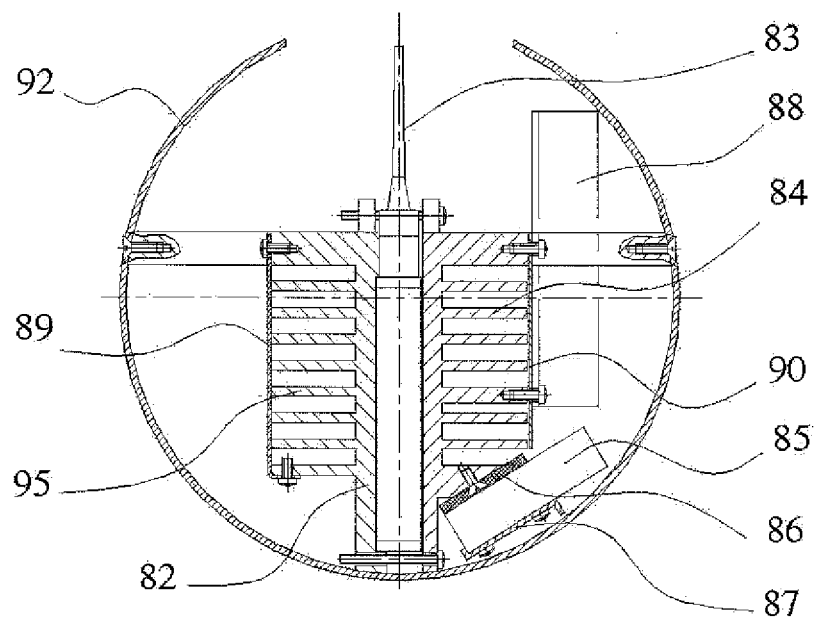
FIG. 2 is a cross-sectional view, taken along line A-A from the FIG. 1, of the embodiment according to the present invention.

The millimeter-wave receiving device may further comprise partitions 89, 90, as shown in FIG. 2, which enclose the radiating fins 95 provided on the third surface 822 and the fourth surface 842 respectively to form air passages. The partitions 89, 90 may be connected to the radiating fins 95 by means of such as threads, welding and riveting to form closed air passages. That is, the air passages may be formed inside the radiating fins 95. Advantageously, the temperature of the air in the air passages is not subjected to affect and influence of the external temperature to a large extent and become stable, and thus the adverse effects of the large fluctuation of the temperature to the detection can be avoided.

In FIG. 1, a fan 91 may be provided at the inlet side or outlet side of the air passages, for improving the heat dissipation accumulated in the air passages from the radiometer 83 or the other components. An air vent 97, which corresponds to the fan 91, may be arranged on the positioning assembly 824 external to the fan 91. Apart from the fan 91, other venting or cooling apparatus may also be used to discharge the heat in the air passages to prevent the temperature around the radiometer 83 from increasing significantly due to heat accumulation.

The millimeter-wave receiving device according to the present invention may further comprise a supporting member 81. The supporting member 81 may be any supporting means which can be fixed on the floor, frame or other devices, for example a bracket, a base. The millimeter-wave receiving device may further comprise an orientation assembly by which the positioning assembly 824 is connected to the supporting member 81. The orientation assembly functions to regulate the orientation of the supporting member 81 relative to the positioning assembly 824, and thus adjust the pitch angle of the radiometer 83 relative to the supporting member 81, to ensure that the radiation receiving direction of the radiometer 83 can meet the requirements for the pitching.

In an embodiment, the orientation assembly may comprise a connection member 811 and an arc-shaped slide opening 810 provided on the supporting member 81, as illustrated in FIG. 1. One end of the connection member 811 is connected to the positioning assembly 824, and the other end is adjustably connected to the supporting member 81. The connection member 811 connects the supporting member 81 with the positioning assembly 824 through the arc-shaped slide opening 810. The connection member 811 is capable of sliding in the arc-shaped slide opening 810 to adjust the pitch angle of the radiometer 83 with respect to the supporting member 81.

The connection member 811 may be, for example, thread connections or pin connections. The connection member 811 can adjust the orientation of the radiometer 83 relative to the supporting member 81 by sliding in the arc-shaped slide opening 810. In operation, the connection member 811 may be set to a slidable state at first, and then it may be slided along the arc-shaped slide opening 810 to a suitable position as required and be fastened to allow the positioning assembly 824 and the radiometer 83 to be held stably in the desired direction.

In an embodiment, as shown in the FIG. 3, the first positioning member 82 may further comprise an extension portion 96 which is provided with holes 820. The connection member 811 may be connected to the holes 820 through an arc-shaped slide opening 810. The extension portion 96 may be arranged at one side, connected to the supporting member 81, of the first positioning member 82. The extension portion 96 may be arranged in such a manner that it can extend along the direction perpendicular to the first surface 821 of the first positioning member 82 from one end of the first positioning member 82. Such extension portion 96 as above may be referred as 90° extension portion. In order to improve the connection between the connection member 811 and the arc-shaped slide opening 810, at least two arc-shaped slide openings may be arranged at one circumference on the supporting member 81 and at least two groups of holes 820 may be arranged at various angles in the extension portion 96. The position of each of the groups of holes 820 correspond to that of each of the arc-shaped slide openings 810.

In FIG. 3, the extension portion 96 has two holes 820 which face two arc-shaped slide openings 810 on the supporting member 81 (see FIG. 1) respectively. In some embodiments, more groups of the holes 820 corresponding to various positions of the arc-shaped slide openings 810 may be used. When the positioning assembly 824 is rotated at a relative large angle with respect to the supporting member 81, one group of holes 820 may fail to be cooperated with the arc-shaped slide opening 810 as it is out of the length range of the arc-shaped slide opening 810. However, as several groups of the holes 820 are provided at various positions at the circumference, even if one group of holes 820 does not fall within the length range of the arc-shaped slide opening 810, the arc-shaped slide opening 810 can still be cooperated with other groups of holes 820. Thus, the orientation of the radiometer 83 may be regulated at an enlarged scope without being limited to the size of the arc-shaped slide openings 810.

Although FIG. 3 only illustrates a group of holes 820, it would be appreciated that two, three or more groups of holes 820 may also be used as long as they can be cooperated with the arc-shaped slide openings 810 at various angular positions.

Although, in the above examples, the orientation of the radiometer 83 is regulated only by means of the relative rotation of the positioning assembly 824 and the supporting member 81 with the cooperation of the arc-shaped slide opening 810 and the holes 820, it should be appreciated that the orientation assembly may be implemented in other forms. For example, it may perform the rotation and fixing between the positioning assembly 824 and the supporting member 81 by means of, for example, friction or pin rolls. All of these means fall within the scope of the present invention.

In an embodiment, the fan 91 may be provided inside the extension portion 96 of the first positioning member 82. Accordingly, the air vent 97 may be arranged in the extension portion 96 corresponding to the fan 91 to facilitate the heat dissipation from the radiometer 83.

Figure 4:
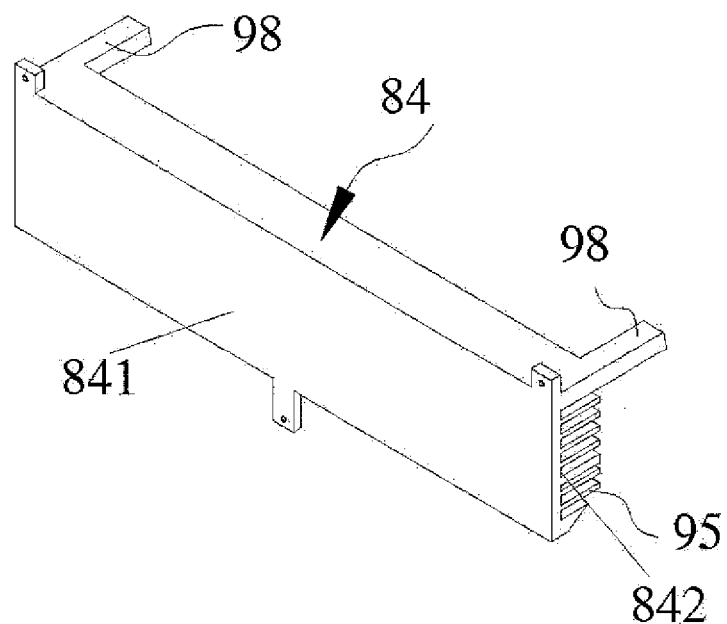
FIG. 4 is a perspective view showing a second positioning member according to an embodiment of the present invention.

As illustrated in FIGS. 1-2, the millimeter-wave receiving device may further comprise a shielding cylinder 92 which surrounds the positioning assembly 824 and the radiometer 83 except a gap in the receiving direction of the radiometer 83. The shielding cylinder 92 may allow the radiometer 83 to receive the millimeter-wave radiation in a certain direction and reduce significantly the interference of the electrical-magnetic radiations to the radiometer 83 from other directions. Thus, it is helpful to improve the detection accuracy of the millimeter-wave receiving device. The shielding cylinder 92 may be held on the positioning assembly 824 by stands 98 of the positioning assembly 824. In FIGS. 3-4, the stands 98 may be provided at various positions on the first positioning member 82 and the second positioning member 84 to achieve the rigidity and stability required for supporting the shielding cylinder 92. The shielding cylinder 92 may be connected to the stands 98 by, such as, threaded connection, welding, riveting.

Figure 5:
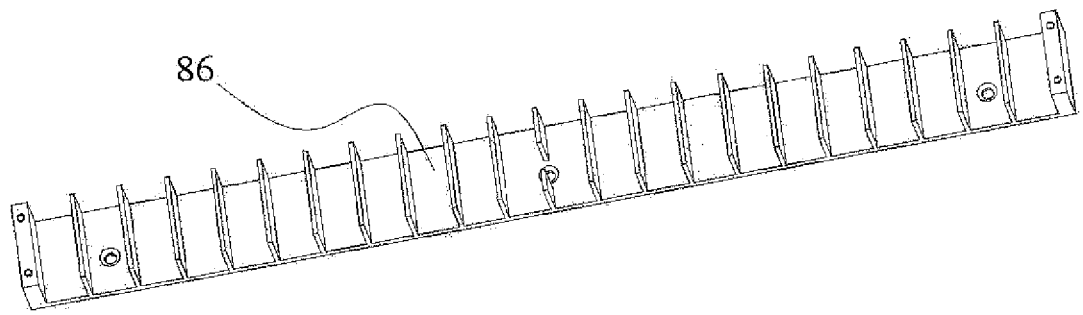
FIG. 5 is a perspective view showing a high frequency amplifier bracket according to an embodiment of the present invention.

As shown in FIG. 6, the millimeter-wave receiving device may further comprise a high frequency amplifier 85 which is used to amplify the signals received by the radiometer 83 in high frequency band to meet the requirement of data sampling. The high frequency amplifier 85 may be fixed on a high frequency amplifier bracket 86. For example, referring to FIG. 5, the high frequency amplifier bracket 86 may have a grid arrangement. Each grid accommodates one high frequency amplifier 85. The high frequency amplifier bracket 86 may be mounted below the fourth surface 842 of the second positioning member 84. A holding plate 87 which presses the high frequency amplifier 85 accommodated in the high frequency amplifier bracket 86 can be further provided.

The millimeter-wave receiving device may further comprise a data sampling board 88 mounded on the positioning assembly 824. The data sampling board 88 is used to sample the signals detected by the radiometer 83 and amplified by the high frequency amplifier 85 for the subsequent analysis and processing.

The high frequency amplifier 85 and the data sampling board 88 may be provided in the millimeter-wave receiving device as above to achieve a compact size of the apparatus. Alternatively, they may be separated from the millimeter-wave receiving device as required.

It is noted that any combinations of the above embodiments also fall within the scope of the present invention. For example, the first positioning member 821 may be provided with any one of more selected from the extension portion 96, the radiating fins 95, the bulged borders 93, the saw-shaped steps 94 and the air vent 97. And the millimeter-wave receiving device may also comprise the orientation assembly including the connection member and the arc-shaped slide opening; positioning members, such as the saw-shaped steps 94; or venting members, such as the radiating fins 95, the partitions 89, 90 and the fan 91.

Although the embodiments of the present invention have been described in conjunction with figures, modifications to the above embodiments can be carried out without departing the spirit of the present invention.

The above technical features or various structures of the present invention can be mutually combined to form new structures. It can be appreciated by those skilled in the art that the combinations fall within the scope of the present invention.

The invention claimed is:
1. A millimeter-wave receiving device, comprising:
at least one radiometer; and
a positioning assembly for holding the radiometer, wherein the positioning assembly comprises:
a first positioning member having a first surface;
a second positioning member having a second surface, the first surface of the first positioning member and the second surface of the second positioning member holding the radiometer in opposite to each other,
wherein the first surface of the first positioning member is formed with a bulged border at its periphery, the bulged border comprising an upper rim and a lower rim, which are formed with at least one group of saw-shaped steps opposed to each other respectively; and
wherein each radiometer includes a positioning portion which matches with its corresponding saw-shaped step, the each radiometer being held on the saw-shaped step by the positioning portion.

2. The millimeter-wave receiving device according to claim 1, wherein the millimeter-wave receiving device comprises a plurality of radiometers which are arranged in a line.

3. The millimeter-wave receiving device according to claim 1, wherein each saw-shaped step has a first step positioning surface and a second step positioning surface,
wherein the first step positioning surfaces of the respective saw-shaped steps are inclined at a same angle with respect to the horizontal direction, and wherein the second step positioning surfaces of the respective saw-shaped steps are inclined at a same angle with respect to the vertical direction.

4. The millimeter-wave receiving device according to claim 1, wherein each saw-shaped step has a first step positioning surface and a second step positioning surface,
wherein the first step positioning surfaces of the respective saw-shaped steps are inclined at different angles with respect to the horizontal direction, and wherein the second step positioning surfaces of the respective saw-shaped steps are inclined at different angles with respect to the vertical direction.

5. The millimeter-wave receiving device according to claim 1, wherein the positioning portion is a limited step or a projection.

6. The millimeter-wave receiving device according to claim 1, wherein the first positioning member further has a third surface opposed to the first surface, and the second positioning member has a fourth surface opposed to the second surface,
wherein the third surface and the fourth surface are provided with a plurality of radiating fins thereon respectively.

7. The millimeter-wave receiving device according to claim 6, wherein the millimeter-wave receiving device further comprises partitions, which enclose the radiating fins provided on the third surface and the fourth surface respectively to form air passages.

8. The millimeter-wave receiving device according to claim 7, wherein a fan is provided at the inlet side or outlet side of the air passages, and an air vent, which corresponds to the fan, is arranged on the positioning assembly external to the fan.

9. The millimeter-wave receiving device according to claim 1, wherein the millimeter-wave receiving device further comprises:
a supporting member; and
an orientation assembly by which the positioning assembly is connected to the supporting member to adjust a pitch angle of the radiometer relative to the supporting member.

10. The millimeter-wave receiving device according to claim 9, wherein the orientation assembly further comprises:
a connection member, one end of which is connected to the positioning assembly, and the other end of which is adjustably connected to the supporting member; and
an arc-shaped slide opening provided on the supporting member,
wherein the connection member connects the supporting member with the positioning assembly through the arc-shaped slide opening, and is capable of sliding in the arc-shaped slide opening to adjust the pitch angle of the radiometer with respect to the supporting member.

11. The millimeter-wave receiving device according to claim 10, wherein the first positioning member further comprises an extension portion provided with holes to which the connection member is connected through the arc-shaped slide opening.

12. The millimeter-wave receiving device according to claim 11, wherein the extension portion extends along the direction perpendicular to the first surface of the positioning member from one end of the first positioning member.

13. The millimeter-wave receiving device according to claim 1, wherein the millimeter-wave receiving device further comprises a shielding cylinder which surrounds the positioning assembly and the radiometer except a gap in the receiving direction of the radiometer, the shielding cylinder being held on the positioning assembly by stands of the positioning assembly.

14. The millimeter-wave receiving device according to claim 1, wherein the millimeter-wave receiving device further comprises:
a high frequency amplifier and a high frequency amplifier bracket having a grid arrangement in which each grid accommodates one high frequency amplifier.

15. The millimeter-wave receiving device according to claim 1, wherein the millimeter-wave receiving device further comprises a data sampling board mounded on the positioning assembly.

* * * * *